United States Patent
Hoernig et al.

(10) Patent No.: US 11,304,666 B2
(45) Date of Patent: Apr. 19, 2022

(54) CREATION OF A DIGITAL TWIN FOR MEDICAL EXAMINATIONS

(71) Applicant: Siemens Healthcare GmbH, Erlangen (DE)

(72) Inventors: Mathias Hoernig, Moehrendorf (DE); Ralf Nanke, Neunkirchen am Brand (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/807,296

(22) Filed: Mar. 3, 2020

(65) Prior Publication Data

US 2020/0281539 A1    Sep. 10, 2020

(30) Foreign Application Priority Data

Mar. 8, 2019   (DE) .......................... 102019203192.7

(51) Int. Cl.
| | |
|---|---|
| A61B 5/00 | (2006.01) |
| A61B 6/00 | (2006.01) |
| A61B 5/055 | (2006.01) |
| A61B 6/03 | (2006.01) |
| G16H 50/50 | (2018.01) |
| G16H 30/40 | (2018.01) |
| G06T 17/00 | (2006.01) |

(52) U.S. Cl.
CPC .............. *A61B 5/744* (2013.01); *A61B 5/055* (2013.01); *A61B 6/032* (2013.01); *A61B 6/461* (2013.01); *G06T 17/00* (2013.01); *G16H 30/40* (2018.01); *G16H 50/50* (2018.01); *G06T 2200/08* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 10,878,639 B2 * | 12/2020 | Douglas | G06T 15/08 |
| 2008/0015418 A1 * | 1/2008 | Jarrell | G09B 5/00 600/300 |
| 2013/0034280 A1 * | 2/2013 | Bernhardt | A61B 6/469 382/128 |
| 2015/0359486 A1 * | 12/2015 | Kovacs | A61B 5/0245 600/301 |
| 2016/0191887 A1 | 6/2016 | Casas | |
| 2018/0338742 A1 | 11/2018 | Singh et al. | |
| 2018/0360543 A1 * | 12/2018 | Roh | G16H 50/20 |
| 2019/0059725 A1 * | 2/2019 | Greiner | A61B 5/002 |
| 2020/0242767 A1 * | 7/2020 | Zhao | A61B 6/50 |
| 2021/0343396 A1 * | 11/2021 | Glatz | G16H 30/20 |

* cited by examiner

*Primary Examiner* — James A Thompson
(74) *Attorney, Agent, or Firm* — Harness, Dickey & Pierce, P.L.C.

(57) ABSTRACT

A method for creating a virtual patient model includes acquiring image data of the patient from a number of directions and in a number of positions of the patient. A virtual patient is created based upon the acquired image data. The virtual patient is adjusted to a posture of the patient during a planned examination with a medical engineering examination apparatus. A patient model creation apparatus is also described. Moreover, a medical engineering examination system is described.

33 Claims, 2 Drawing Sheets

CREATION OF A DIGITAL TWIN FOR MEDICAL EXAMINATIONS

PRIORITY STATEMENT

The present application hereby claims priority under 35 U.S.C. § 119 to German patent application number DE 102019203192.7 filed Mar. 8, 2019, the entire contents of which are hereby incorporated herein by reference.

FIELD

At least one embodiment of the invention generally relates to a method for creating a virtual patient model. At least one embodiment of the invention also generally relates to a patient model creation apparatus. Moreover, at least one embodiment of the invention generally relates to a medical engineering examination system.

BACKGROUND

With medical examinations with the aid of medical engineering devices, for instance imaging apparatuses, data of the patient is required in advance in order to be able to carry out the examination process correctly. For instance, in order to prepare a CT system for an imaging process, data has to be captured in order to determine recording parameters, to determine weight and to determine the permitted dose and to capture a specific organ region to be imaged. Capturing this data is time-consuming and requires high staffing levels.

Nowadays with CT imaging it is usual to record an overview image of the patient, when he has already taken a seat on the patient couch, the overview image having in most cases just two-dimensional contours or being recorded only from one direction. An accurate determination of the dimensions of the body of a patient is therefore not possible.

SUMMARY

At least one embodiment of the present invention enables a more precise and simplified adjustment of an examination process to specific properties of a patient with the aid of a medical engineering apparatus.

Embodiments of the present invention are directed to a method for creating a virtual patient model, a patient model creation apparatus and a medical engineering examination system.

With at least one embodiment of the inventive method for creating a virtual patient model, image data of the patient is acquired from several directions and preferably also in a number of positions of the patient. In this context, sensor data which enables an at least two-dimensional imaging of an object is to be understood as image data. Image data can therefore comprise in particular visual data, but also terahertz sensor data, thermal image data, ultrasound data or other sensor data which can be used for imaging an object. A virtual patient is created on the basis of the obtained image data. One such virtual patient comprises a digital 3D model of a patient, which is individualized on the basis of the captured image data. One such model is also referred to as digital twin, avatar, virtual twin or virtual patient model. The model can have network point-type surface data of a patient or a part of a patient which is based on visual recognition or general sensor recognition. It can also contain additional data of the inside of the patient, such as for instance information relating to the position and orientation of organs, joints or skeleton data. Finally, the virtual patient is automatically adjusted to a posture of the patient during a planned examination with a medical engineering examination apparatus. The adjustment of the virtual patient can take place for instance on the basis of the newly obtained, updated image data of the patient.

At least one embodiment of the inventive patient model creation apparatus has an acquisition unit for acquiring image data of the patient from several directions and in several positions of the patient. The acquisition unit can comprise, for instance, an input interface which receives image data from a database or from image recording units, such as cameras, for instance. Image data can be used both in advance for model creation and also for subsequent adaptation of the digital twin or virtual patient to a current position and location or alignment of the patient. Part of At least one embodiment of the inventive patient model creation apparatus is also a model creation unit for creating a virtual patient on the basis of the obtained image data. The inventive patient model creation apparatus also has an adaptation unit for adjusting the virtual patient to a posture of the patient in the case of a planned examination with a medical engineering examination apparatus. At least one embodiment of the inventive patient model creation apparatus shares the advantages of at least one embodiment of the inventive method for creating a virtual patient model.

At least one embodiment of the inventive medical engineering examination system has a medical engineering imaging apparatus, a region to be entered by a patient to be examined on the way to the medical engineering imaging apparatus, the inventive patient model creation apparatus and a plurality of image recording units, which are directed at the region to be entered by the patient to be examined from different directions.

A realization partially through software has the advantage that computer systems already used until now in CT systems when supplementing with hardware units in order to record image data of the patient can be easily upgraded with a software update in order to operate in the inventive manner. In this respect, at least one embodiment of the invention is also directed to a corresponding computer program product with a computer program which is loadable directly into a storage apparatus of such a computer system, having program portions in order to carry out all the steps of the method of at least one embodiment for creating a virtual patient model when the computer program is executed in the computer system.

At least one embodiment is directed to a method for creating a virtual patient, comprising:

acquiring image data of a patient from a number of directions;

creating a virtual patient based upon the image data acquired; and adjusting the virtual patient created to a posture of the patient during a planned examination, using a medical engineering examination apparatus.

At least one embodiment is directed to a method for creating a virtual patient, comprising:

acquiring image data of a patient from a number of directions; and creating the virtual patient based upon the image data acquired, the virtual patient created being adjustable, via a medical engineering examination apparatus, to a posture of the patient during a planned examination.

At least one embodiment is directed to a virtual patient creation apparatus, comprising:

an acquisition unit to acquire image data of a patient from a number of directions and in a number of positions of the patient;

a model creation unit to create the virtual patient based upon the image data acquired; and an adaptation unit to adjust the virtual patient created to a posture of the patient during a planned examination via a medical engineering examination apparatus.

At least one embodiment is directed to a medical engineering examination system, comprising:

a medical engineering examination apparatus;

a region to be entered by the patient to be examined on a way to the medical engineering examination apparatus;

a virtual patient creation apparatus of an embodiment; and a plurality of image recording units, directed to a plurality of various directions at the region to be entered by the patient to be examined.

At least one embodiment is directed to a non-transitory computer program product storing a computer program, directly loadable into a storage unit of a medical engineering examination system, including program portions to carry out the method of an embodiment, when the computer program is carried out in the medical engineering examination system.

At least one embodiment is directed to a non-transitory computer-readable medium storing program portions, executable by a computer unit, the program portions carrying out the method of an embodiment when the program portions are executed by the computer unit.

At least one embodiment is directed to a virtual patient creation apparatus, comprising:

at least one camera to acquire image data of a patient from a number of directions and in a number of positions of the patient; and at least one processor to create the virtual patient based upon the image data acquired and to adjust the virtual patient, via a medical engineering examination apparatus, created to a posture of the patient during a planned examination.

The claims and the description below each contain particularly advantageous embodiments and developments of the invention. Here the claims of one claim category can in particular also be developed analogously to the dependent claims of another claim category. In addition, in the context of embodiments of the invention, the different features of different example embodiments and claims can also be combined to form new example embodiments.

BRIEF DESCRIPTION OF THE DRAWINGS

The invention is explained again in more detail below with reference to the appended figures on the basis of example embodiments, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor;

however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With at least one embodiment of the inventive method for creating a virtual patient model, image data of the patient is acquired from several directions and preferably also in a number of positions of the patient. In this context, sensor data which enables an at least two-dimensional imaging of an object is to be understood as image data. Image data can therefore comprise in particular visual data, but also terahertz sensor data, thermal image data, ultrasound data or other sensor data which can be used for imaging an object. A virtual patient is created on the basis of the obtained image data. One such virtual patient comprises a digital 3D model of a patient, which is individualized on the basis of the captured image data. One such model is also referred to as digital twin, avatar, virtual twin or virtual patient model. The model can have network point-type surface data of a patient or a part of a patient which is based on visual recognition or general sensor recognition. It can also contain additional data of the inside of the patient, such as for instance information relating to the position and orientation of organs, joints or skeleton data. Finally, the virtual patient is automatically adjusted to a posture of the patient during a planned examination with a medical engineering examination apparatus. The adjustment of the virtual patient can take place for instance on the basis of the newly obtained, updated image data of the patient.

For instance, here a patient position on the examination couch can be acquired by cameras and this current additional information can be used to adjust the digital twin. The medical engineering examination apparatus can comprise for instance a medical engineering imaging apparatus, particularly preferably an x-ray system or an MR system.

Improved accuracy of the patient model is advantageously achieved by the adjustment process. For instance, the contour and weight of the model correspond rather to the actual conditions, but information relating to the inner properties of the body of the patient or his state of health can also be taken into account when the digital twin is created. Due to the improved precision of the digital twin, it is possible to refine the positioning of the patient and the setting of the system parameters. Due to the exact knowledge of the contours of the patient, the resolution requirements on any available cameras of the medical engineering examination apparatus can be reduced in order to recognize the final location of the patient on a patient couch. Particularly advantageously the patient model can be used for the adjusted avatar calculation of the current location of the patient, if the patient is disposed in the final examination position, for instance for lateral recordings or with angled arms.

At least one embodiment of the inventive patient model creation apparatus has an acquisition unit for acquiring image data of the patient from several directions and in several positions of the patient. The acquisition unit can comprise, for instance, an input interface which receives image data from a database or from image recording units, such as cameras, for instance. Image data can be used both in advance for model creation and also for subsequent adaptation of the digital twin or virtual patient to a current position and location or alignment of the patient. Part of At least one embodiment of the inventive patient model creation apparatus is also a model creation unit for creating a virtual patient on the basis of the obtained image data. The inventive patient model creation apparatus also has an adaptation unit for adjusting the virtual patient to a posture of the patient in the case of a planned examination with a medical engineering examination apparatus. At least one embodiment of the inventive patient model creation apparatus shares the advantages of at least one embodiment of the inventive method for creating a virtual patient model.

At least one embodiment of the inventive medical engineering examination system has a medical engineering imaging apparatus, a region to be entered by a patient to be examined on the way to the medical engineering imaging apparatus, the inventive patient model creation apparatus and a plurality of image recording units, which are directed at the region to be entered by the patient to be examined from different directions.

A region to be entered can comprise a changing room, for instance, which has to be located by the patient before locating the medical engineering imaging apparatus in order to store clothing. The region to be entered can comprise, for instance, a region to be traversed, such as, for instance, an access path to the medical engineering imaging apparatus. The inventive medical engineering examination system shares the advantages of the inventive patient model creation apparatus. Advantageously the image data can moreover be captured from the patient virtually in passing, without involving additional effort for the patient.

Parts of at least one embodiment of the inventive patient model creation apparatus can be configured mainly in the form of software components. This relates in particular to parts of the acquisition unit, the model creation unit and the adaptation unit. Essentially these components can however also be realized to some extent, particularly if particularly rapid calculations are involved, in the form of software-assisted hardware, for instance FPGAs or suchlike. Similarly the required interfaces, for instance when only a takeover of data from other software components is involved, can be embodied as software interfaces. They can however also be configured as interfaces constructed from hardware, which are controlled by suitable software.

A realization partially through software has the advantage that computer systems already used until now in CT systems when supplementing with hardware units in order to record image data of the patient can be easily upgraded with a software update in order to operate in the inventive manner. In this respect, at least one embodiment of the invention is also directed to a corresponding computer program product with a computer program which is loadable directly into a storage apparatus of such a computer system, having program portions in order to carry out all the steps of the method of at least one embodiment for creating a virtual patient model when the computer program is executed in the computer system.

Such a computer program product can comprise, where relevant, in addition to the computer program, further constituents, such as, for example, documentation and/or additional components including hardware components such as, for example, hardware keys (dongles, etc.) in order to use the software.

For transport to the storage apparatus of the computer system and/or for storage at the computer system, a computer-readable medium, for example, a memory stick, a hard disk or another transportable or permanently installed data carrier can be used on which the program portions of the computer program which can be read in and executed by a computer unit are stored. For this purpose, the computer unit can have, for example, one or more cooperating microprocessors or the like.

The claims and the description below each contain particularly advantageous embodiments and developments of the invention. Here the claims of one claim category can in particular also be developed analogously to the dependent claims of another claim category. In addition, in the context of embodiments of the invention, the different features of different example embodiments and claims can also be combined to form new example embodiments.

With a particularly preferred development of embodiments of the inventive method for creating a virtual patient model, the medical engineering examination apparatus is set automatically for an image recording of the patient on the basis of parameter data of the virtual patient. Advantageously the medical engineering examination apparatus can be set on the basis of the data of the adapted virtual patient model without intervention by medical personnel, so that the preparation of an examination is simplified, less manpower-intensive, quicker and more cost-effective.

In one embodiment of the inventive method for creating a virtual patient model, the image data of the patient is acquired automatically, while the patient is approaching the medical engineering examination apparatus. Advantageously the data required for creating the virtual patient model can be captured in effect in passing, without involving an additional time requirement or an additional load for the patient. The data acquisition can also be carried out within the scope of a changing process of the patient or another necessary preparation or preexamination process, wherein the patient need not however pay any consideration to the image recording and also need not apply any cooperation. Patient comfort is thus improved, furthermore there is no additional time required for the data acquisition so that the entire examination process is accelerated.

In a special embodiment of the inventive method for creating a virtual patient model, at least one of the following technical apparatuses is used to acquire the image data:
an optical image capture apparatus,
an image capture apparatus based on the terahertz technology,
an infrared imaging apparatus.

An optical image capture apparatus or an infrared imaging apparatus can comprise a camera, for instance. Advantageously such sensor data has a high resolution, in order also to determine details of the shape of a patient exactly.

In one variant of the inventive method for creating a virtual patient model, the optical image capture apparatus comprises at least one of the following technical apparatuses:
a 2D camera,
a 3D camera.

If 2D cameras are used, at least two of these image cameras must be employed in order to be able to create a three-dimensional virtual patient model from the 2D image data.

The acquisition of the image data is preferably carried out by applying a combination of at least two different types of the cited technical apparatuses. Additional information can be captured from a patient advantageously with the aid of different technologies.

For instance, the outer shape of the patient can be captured by optical cameras. In addition, information relating to the interior of the patient can be determined with the aid of a thermal imaging system. In this way the blood flow through a body region can be determined, for instance.

Terahertz imaging can be used to capture the body shape of dressed persons. The use of terahertz imaging or a thermal camera renders the calculation of an avatar model of the current location of a patient on the patient couch clearly easier, if for instance the arm of the patient is at an angle and in particular if parts of the patient are covered by clothing, surgery cloths or coils.

Within the scope of at least one embodiment of the inventive method for creating a virtual patient model, the virtual patient can also be created on the basis of an individual virtual patient model which is already stored in advance. In this variant, the virtual patient model is updated in real time on the basis of the acquired image data. Advantageously already available model data can be used, so that the creation of the virtual patient model can be accelerated still further.

Furthermore, with at least one embodiment of the inventive method for creating a virtual patient model, the acquisition of the image data and/or the creation of a virtual patient is adjusted to an organ program or a specific procedure. Advantageously for instance a higher resolution can be fixed in the region of the virtual patient to be examined as a function of the organ program or the planned examination. On account of this measure, a more precise adaptation of the examination to the patient can take place and the data processing effort is however restricted to the required measure.

In one variant of the inventive method for creating a virtual patient model, the position and orientation of the apparatuses employed to acquire the image data are fixed automatically as a function of the planned specific procedure. For instance, image recording apparatuses are positioned so that a body region which is relevant to the specific examination procedure can be captured particularly well, so that this region can be captured with high detail in particular.

With the acquisition of the image data, the operating personnel of the medical engineering examination apparatus can additionally be captured and the medical engineering examination apparatus can also be set on the basis of the image data of the operating personnel. Image data of the operating personnel can be used, for instance, to determine the shape or even skills, responsibilities or competencies of the personnel. Advantageously the automated setting of the medical engineering examination apparatus can thus be adjusted to the shape and skills of the operating personnel, so that operation of the medical engineering examination apparatus can be facilitated herefor.

Figure 1:
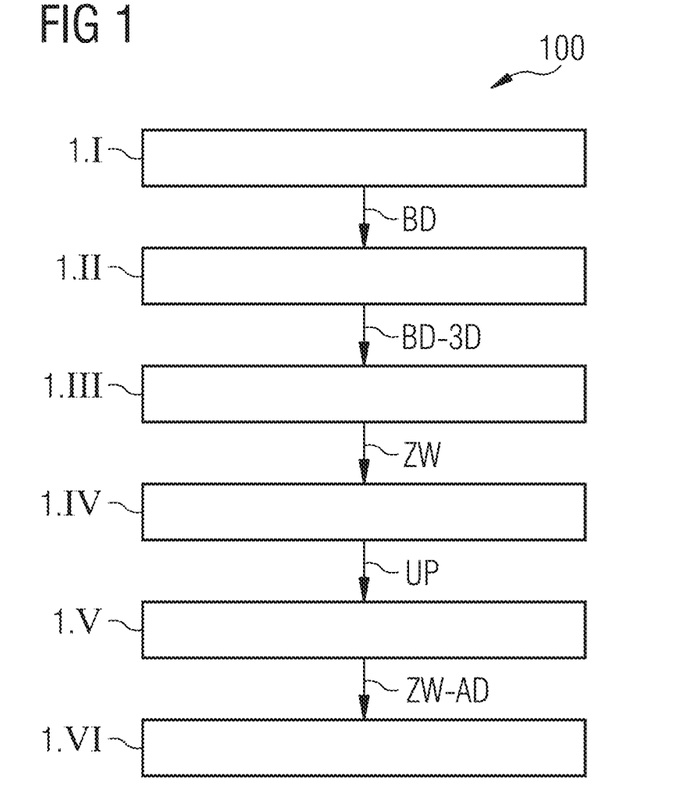
FIG. 1 shows a flow chart, which illustrates a method for creating a virtual patient model according to an example embodiment of the invention.

FIG. 1 shows a flow chart 100, which illustrates a method for creating a digital twin according to an example embodiment of the invention. The scenario underlying the method is as follows: a patient P is to be examined with the aid of a CT system. Here an image recording is to be created of a specific body region, for instance the heart, in order to be able to determine the state of the coronary vessels of the heart.

In step 1.I, the patient locates a changing room, which is disposed in a vestibule of the actual examination region. He undresses there. During this process, the patient is already imaged from several directions and in different positions. In step 1.II the image data BD created in the process is used to create three-dimensional image data BD-3D of the patient. In step 1.I, additional information about the patient is also captured with the aid of a terahertz scanner. For instance, information about whether the patient P is wearing a prosthesis, and on which point on his body this is located can be obtained with the aid of this device. Further information relating to the patient can be obtained with the aid of a thermal imaging camera. By way of example, the blood flow through the patient or center of inflammation in his body can be determined.

In step 1.II, the technology of 3D scatter plot fusion is applied in order to obtain the 3D image data. A scatter plot is a set of points in a vector space which has a disorganized spatial structure (scatter). A scatter plot is described by the contained points, which are each captured by their spatial coordinates. The creation can essentially be carried out by way of scanning methods or photogrammetric methods and in general by way of sampling object surfaces by systems such as coordinate measuring machines or sampling 3D scanners. By way of example, a number of 3D cameras attached in the room are used, of which each camera produces a scatter plot of the patient, for instance. For a higher accuracy (e.g. by way of angular coverage, front-rear-sides), the scatter plots of these cameras are fused with one another.

In step 1.III a digital twin ZW of the patient P is created as a patient model on the basis of the three-dimensional image data BD-3D. In step 1.IV, examination protocol data UP is now received by a control computer 34 (see FIG. 3) which is used to control the CT system. This examination protocol data UP comprises for instance information about the condition and position of the patient on a patient couch of the CT system. Furthermore, the examination protocol data UP also comprises information about the organ region to be captured, recording parameters and the dose determination. The cited information is used in step 1.V to adjust the digital twin ZW to the specific examination situation. Thereupon the digital twin ZW is adapted to the examination position of the patient P defined in the examination protocol UP. For instance, the patient is brought into a position and orientation which corresponds to the examination protocol UP. The capture of the actual position location/orientation in the examination position is then carried out in a sub-step with cameras. The remaining data UP of the examination protocol is also used to adjust the digital twin ZW to the planned examination situation. The current position data of the patient can also be acquired continuously by the cameras and position changes (movements etc.) of the patient can thus be detected. These changes are then likewise transmitted to the digital twin, so that current information about the position, the location and the state of the patient is always available.

In step 1.VI, the medical engineering system is now adjusted to the digital twin ZW. For instance, an x-ray dose is selected according to the shape and the body type of the patient P. Many other recording parameters are also adjusted to the shape of the patient P. Furthermore, for instance in the case that the patient P wears a prosthesis, measures are taken to suppress artifacts, which are caused by the material of the prosthesis.

Figure 2:
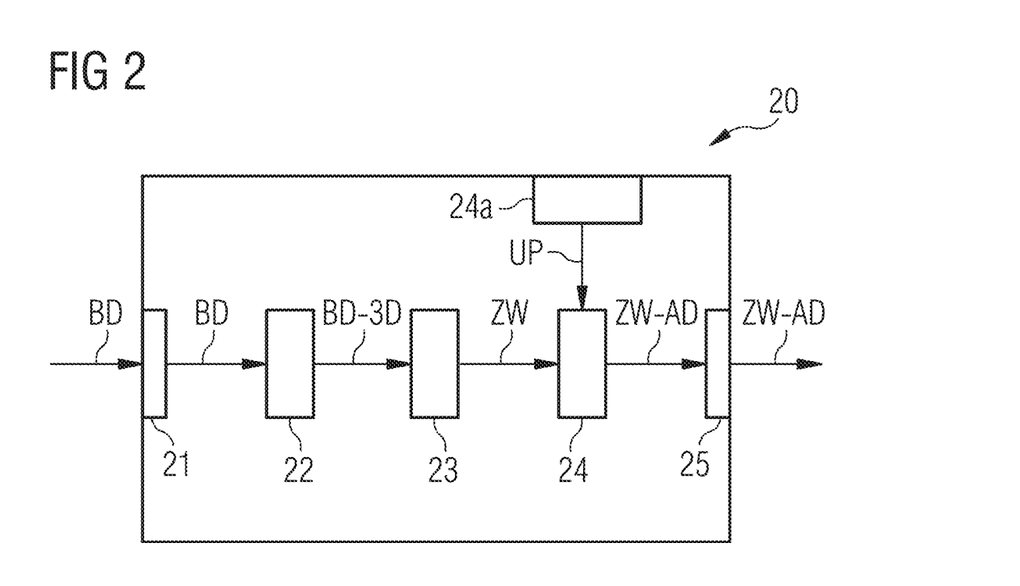
FIG. 2 shows a schematic representation of a patient model creation apparatus according to an example embodiment of the invention.

FIG. 2 illustrates a schematic representation of a patient model creation apparatus 20 according to an example embodiment of the invention. The patient model creation apparatus 20 comprises an input interface 21 as an acquisition unit for receiving image data BD of a plurality of image cameras 33 (see FIG. 3). The received image data BD is transmitted to a 3D image creation unit 22 which creates three-dimensional image data BD-3D on the basis of the initially only two-dimensional image data BD. The three-dimensional image data BD-3D is transmitted to a model creation unit 23, which is designed to create a virtual patient ZW on the basis of the obtained image data BD. The data of the virtual twin ZW is transferred to an adaptation unit 24. The adaptation unit 24 receives, via an interface 24a to a CT system 31 (see FIG. 3), examination protocol data UP from the control of the CT system. The examination protocol data UP is used to adjust the posture of the digital twin ZW and further parameters to a posture of the patient P in a planned examination with a medical engineering examination apparatus, in this specific example embodiment a CT system. In addition, image data of cameras, which show the actual position of the patient, can also be used to adjust the posture of the digital twin ZW of the digital twin to the actual situation. For instance, the position and location of the patient can deviate from a protocol position which is compensated by the additional image information.

The data relating to the adapted digital twin ZW-AD is output via an output interface 25. For instance, the adapted digital twin ZW-AD is transmitted to a control computer of the CT system which also stores the imaging protocol. The imaging protocol or patient examination protocol UP available in the control computer is then adjusted to the adapted digital twin ZW-AD.

Figure 3:
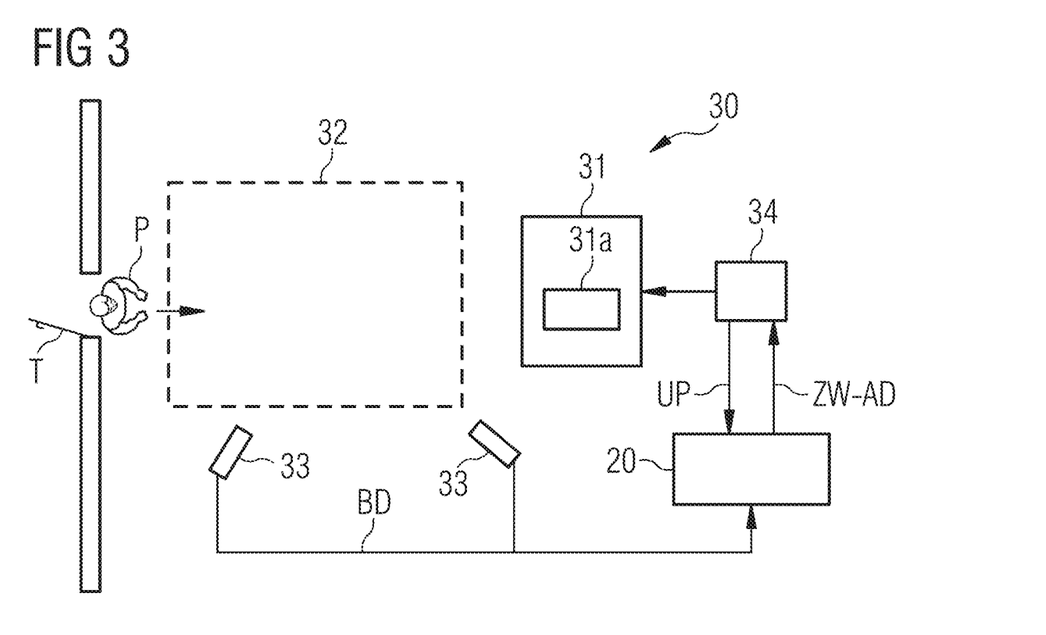
FIG. 3 shows a schematic representation of a medical engineering examination system according to an example embodiment of the invention.

FIG. 3 illustrates a schematic representation of a medical engineering examination system 30 according to an example embodiment of the invention. The medical examination system 30 is located in a room which can be entered via a door T, which is located at the left edge of the pictorial representation. The examination system 30 comprises an imaging device, in this specific example embodiment a CT system 31 with a patient couch 31a. Part of the examination system 30 is also a region 32 to be crossed by a patient P, which the patient P crosses after entering the examination space. Cameras 33 are positioned at the edge of the region 32 to be crossed and capture this region 321 pictorially from different directions. If the patient P crosses this region 32, image data BD of him is automatically acquired from different directions. The image data BD is transmitted to a patient model creation apparatus 20, which creates an adapted digital twin ZW-AD of the patient P in the manner described in conjunction with FIG. 1 and FIG. 2. This adapted digital twin ZW-AD is transmitted to a control computer 34, which adjusts the examination protocol UP on the basis of the adapted digital twin and controls the imaging with the CT system. The patient P takes a seat on the patient couch 31a of the CT system 31 before starting the examination. In addition to the position of the patient P on the patient couch 31a defined by the examination protocol, if the target information is too imprecise for an exact acquisition, the actual position can be determined by additional cameras (not shown). On the basis of the actual position captured in this way and possibly deviating slightly from the protocol position, the data ZW-AD, which relates to the digital twin, can then be adjusted to the position of the patient P on the patient couch 31a which is specific to the subsequent examination.

Finally, it should again be noted that the methods and devices described above are merely preferred example embodiments of the invention and that the invention can be modified by a person skilled in the art without departing from the field of the invention, insofar as it is specified by the claims. For the sake of completeness, it should also be noted that the use of the indefinite articles "a" or "an" does not preclude the relevant features from also being present plurally. Similarly, the expression "unit" does not preclude this consisting of a plurality of components which can possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method comprising:
    acquiring image data of a patient from a number of directions;
    creating a virtual patient based on the image data, the virtual patient being adjustable, via a medical engineering examination apparatus, to a posture of the patient during a planned examination of the patient, and the virtual patient being adjustable based on an examination protocol for the planned examination, wherein
        the medical engineering examination apparatus is a medical imaging apparatus, and
        the planned examination of the patient is a medical imaging of the patient using the medical imaging apparatus; and
    automatically setting, for the medical imaging of the patient, at least one image acquisition parameter of the medical imaging device apparatus, for the planned examination, based on parameter data of the virtual patient.

2. The method of claim 1, wherein the acquiring image data of the patient is carried out for a number of different positions of the patient.

3. The method of claim 2, wherein the virtual patient is automatically adjustable via the medical engineering examination apparatus.

4. The method of claim 1, wherein the acquiring acquires the image data of the patient automatically while the patient is approaching the medical engineering examination apparatus.

5. The method of claim 1, wherein at least one technical apparatus is used in the acquiring image data, the at least one technical apparatus including at least one of:
    an optical image capture apparatus,
    an image capture apparatus based on terahertz technology, or
    an infrared imaging apparatus.

6. The method of claim 5, wherein the optical image capture apparatus comprises at least one of:
    a 2D camera, or
    a 3D camera.

7. The method of claim 5, wherein the acquiring image data comprises:
    applying a combination of at least two different ones of the at least one technical apparatus.

8. The method of claim 1, wherein
    the creating creates the virtual patient based on a previously saved individual virtual patient model, and
    the method further includes updating the virtual patient in real time based on the image data.

9. The method of claim 1, wherein at least one of the acquiring image data or the creating a virtual patient is adjusted to an organ program or a specific procedure.

10. The method of claim 9, wherein a position and an orientation of apparatuses used in the acquiring image data are automatically defined as a function of a specific planned procedure.

11. The method of claim 1, wherein with the acquiring image data, image data of operating personnel of the medical engineering examination apparatus are additionally acquired and the medical engineering examination apparatus is set based on the image data of the operating personnel.

12. The method of claim 1, wherein the virtual patient is automatically adjustable via the medical engineering examination apparatus.

13. The method of claim 1, wherein the at least one image acquisition parameter includes at least one of an x-ray dose, recording parameters for the medical engineering examination apparatus or system parameters for the medical engineering examination apparatus.

14. An apparatus, comprising:
    a medical imaging modality to perform a planned medical imaging examination of a patient according to at least one image acquisition parameter;
    an acquisition unit to acquire image data of the patient from a number of directions and in a number of positions of the patient;
    a model creation unit to create a virtual patient based on the image data; and
    an adaptation unit to adjust the virtual patient to a posture of the patient during the planned medical imaging examination of the patient via the medical imaging modality, the virtual patient being adjustable based on an examination protocol for the planned medical imaging examination, wherein
        the at least one image acquisition parameter is automatically set based on parameter data of the virtual patient.

15. The apparatus of claim 14, wherein the acquisition unit is configured to acquire the image data for a number of different positions of the patient.

16. The apparatus of claim 14, wherein the adaptation unit is configured to automatically adjust the virtual patient.

17. The apparatus of claim 14, wherein the acquisition unit is configured to automatically acquire the image data while the patient is approaching the medical imaging modality.

18. The apparatus of claim 12, wherein the virtual patient is created based on a previously saved individual virtual patient model, and the virtual patient is updated in real time based on the image data.

19. The apparatus of claim 14, wherein the at least one image acquisition parameter includes at least one of an x-ray dose, recording parameters for the medical imaging modality or system parameters for the medical imaging modality.

20. A medical engineering examination system, comprising:
    the apparatus of claim 14;
    a region to be entered by the patient on the way to the medical imaging modality; and
    a plurality of image recording units, directed in a plurality of various directions at the region to be entered by the patient.

21. A non-transitory computer program product storing a computer program, directly loadable into a storage unit of a medical engineering examination system, the computer program including program portions to carry out the method of claim 1, when the computer program is carried out in the medical engineering examination system.

22. A non-transitory computer-readable medium storing program portions, executable by a computer unit, the program portions carrying out the method of claim 1 when the program portions are executed by the computer unit.

23. A method comprising:
acquiring image data of a patient from a number of directions;
creating a virtual patient based on the image data, the virtual patient being adjustable based on an examination protocol for a planned examination of the patient using a medical engineering examination apparatus, wherein
the medical engineering examination apparatus is a medical imaging apparatus, and
the planned examination of the patient is a medical imaging of the patient using the medical imaging apparatus;
adjusting the virtual patient to a posture of the patient during the planned examination, using the medical engineering examination apparatus; and
automatically setting, for the medical imaging of the patient, at least one image acquisition parameter of the medical imaging apparatus, for the planned examination, based on parameter data of the virtual patient.

24. The method of claim 23, wherein the acquiring image data of the patient is carried out for a number of different positions of the patient.

25. The method of claim 23, wherein the virtual patient is automatically adjustable via the medical engineering examination apparatus.

26. The method of claim 23, wherein the acquiring acquires the image data of the patient automatically while the patient is approaching the medical engineering examination apparatus.

27. The method of claim 23, wherein
the creating creates the virtual patient based on a previously saved individual virtual patient model, and
the method further includes updating the virtual patient in real time based on the image data.

28. An apparatus, comprising:
a medical imaging modality to perform a planned medical imaging examination of a patient according to at least one image acquisition parameter;
at least one camera to acquire image data of the patient from a number of directions and in a number of positions of the patient; and
at least one processor to
create a virtual patient based on the image data,
adjust the virtual patient to a posture of the patient during the planned medical imaging examination of the patient, the virtual patient being adjustable based on an examination protocol for the planned medical imaging examination, and
automatically set the at least one image acquisition parameter based on parameter data of the virtual patient.

29. The apparatus of claim 28, wherein the at least one camera is configured to acquire the image data of the patient for a number of different positions of the patient.

30. The apparatus of claim 28, wherein the at least one processor is configured to automatically adjust the virtual patient.

31. The apparatus of claim 28, wherein the at least one camera is configured to automatically acquire the image data while the patient is approaching the medical imaging modality.

32. The apparatus of claim 28, wherein the virtual patient is created based on a previously saved individual virtual patient model, and the virtual patient is updated in real time based on the image data.

33. The apparatus of claim 28, wherein the at least one image acquisition parameter includes at least one of an x-ray dose, recording parameters for the medical imaging modality or system parameters for the medical imaging modality.

* * * * *